United States Patent
Ingram

(10) Patent No.: US 10,575,943 B2
(45) Date of Patent: Mar. 3, 2020

(54) VISION CORRECTION SYSTEMS AND METHODS FOR USING AN INTRAOCULAR LENS ENCLOSED IN AN INNER CAPSULATED BAG

(71) Applicant: Ronald William Ingram, Midland, TX (US)

(72) Inventor: Ronald William Ingram, Midland, TX (US)

(*) Notice: Subject to any disclaimer, the term of this patent is extended or adjusted under 35 U.S.C. 154(b) by 0 days.

(21) Appl. No.: 15/287,969

(22) Filed: Oct. 7, 2016

(65) Prior Publication Data

US 2018/0098841 A1   Apr. 12, 2018

(51) Int. Cl.
*A61F 2/16* (2006.01)

(52) U.S. Cl.
CPC .. *A61F 2/1627* (2013.01); *A61F 2002/16901* (2015.04)

(58) Field of Classification Search
CPC ................. A61F 2/1627; A61F 2/1662; A61F 2002/1681; A61F 2/1629; A61F 2/1632; A61F 2/1694; A61F 2002/169; A61F 2002/16901; A61F 2002/16902
See application file for complete search history.

(56) References Cited

U.S. PATENT DOCUMENTS

| | | | |
|---|---|---|---|
| 2005/0182490 A1* | 8/2005 | McDonald | A61F 2/1618 623/6.27 |
| 2013/0131796 A1* | 5/2013 | Mirlay | A61F 2/1624 623/6.34 |

* cited by examiner

*Primary Examiner* — David H Willse
*Assistant Examiner* — Tiffany P Shipmon
(74) *Attorney, Agent, or Firm* — Hubbard Johnston, PLLC

(57) ABSTRACT

A intraocular lens system includes an artificial capsular bag adapted for implantation within a natural capsular bag of an eye and an intraocular lens adapted to be received within the artificial capsular bag. At least a portion of the intraocular lens tilts and moves forwards within the artificial capsular bag under gravitational force with respect to a cornea and retina of the eye to create myopia.

20 Claims, 10 Drawing Sheets

DISTANCE FOCUS    NEAR FOCUS

VISION CORRECTION SYSTEMS AND METHODS FOR USING AN INTRAOCULAR LENS ENCLOSED IN AN INNER CAPSULATED BAG

FIELD OF INVENTION

The present invention relates in general to ophthalmological surgery, and in particular to vision correction systems and methods using an intraocular lens enclosed in an inner capsulated bag.

BACKGROUND OF INVENTION

Intraocular lenses are typically implanted into the human eye after cataract removal, as well as to correct large refractive errors, such as myopia (nearsightedness), hyperopia (farsightedness), and presbyopia (farsightedness due to the loss of crystalline lens elasticity with age). In aphakic implant surgery, which is commonly used during cataract removal, an opening is made through the anterior portion of the capsular bag surrounding the clouded crystalline lens, the lens is removed, and an intraocular lens is inserted into the remaining portion of the capsular bag. During phakic implantation, the intraocular lens is inserted without removal of the natural lens, typically to correct large refractive errors.

Since the first introduction of the intraocular lens in 1949, the intraocular lens technology has expanded significantly, with the introduction of different optics (e.g., biconvex, convex-plano, spherical, aspherical), new haptics (i.e., structures for holding the intraocular lens within the capsular bag), and improved materials. The earliest lenses were monofocal, which only set a single focal point, which provided near visual acuity or distance visual acuity, but not both. Newer intraocular lens, such as multifocal and accommodating lens, attempt to provide both near visual acuity and distance visual acuity, although they are subject to some significant drawbacks.

Multifocal lens generally consist of circular center zone and a series of concentric rings of varying widths, each of which is intended to provide focus under a particular set of circumstances. In a representative multifocal lens, the center zone is the bright light/distance dominant zone, which provides focus at distance and under bright light conditions (i.e., when the pupil is constricted). The first ring moving outward is the near-dominant zone, which provides additional near vision focus under moderate to low lighting. The distance/intermediate zone is the second ring moving outward and is intended to provide distance vision in a range of light conditions. The next ring out is the near-dominant zone and is intended to provide near vision under a range of light conditions. The outer most ring is the low light/distance-dominant zone, which is intended to provide focus at distance in low light conditions (i.e., when the pupil is dilated).

Multifocal lens are subject to a number of disadvantages. Among other things, since multifocal lenses typically have two focal points (i.e., near and distance), focus at intermediate points can be compromised. Furthermore, the transitions between zones can result in halos and glare in high-contrast lighting situations, such as driving at night. Finally, multifocal lenses are generally not suitable for persons working with fine details, such as reading small print or manipulating small objects.

Accommodating lenses are based on another design intended to provide focus over a range of distances. Generally, accommodating lenses have a single focal point and then employ a pair of hinges, which allow the eye muscles to move the lens forward and backward and thereby shift the focal point as needed to focus on objects of varying distances. In other words, accommodating lenses attempt to emulate the mechanics of a natural crystalline lens. However, while accommodating lenses have been shown to provide good distance visual acuity (i.e., the ability to discern details at distance), near distance acuity has been found to be variable.

SUMMARY OF INVENTION

The principles of the present invention are embodied in vision correction systems and methods in which an inner (artificial) capsular bag and enclosed intraocular lens are inserted within the natural capsular bag of the eye. The inner capsular bag prevents the natural capsular bag from collapsing around the intraocular lens, which allows at least a part of the intraocular lens to move. Specifically, the intraocular lens is configured such that at least part of the intraocular lens can tilt and/or move forward, with respect to the cornea and retina, in response to gravitational force to create myopic astigmatism.

In other words, when the wearer is looking straight forward, the intraocular lens, which preferably includes a monofocal optic, remains substantially vertical within the eye to provide good distance acuity. When the wear looks downward, for example while reading, the resulting tilt of the optic of the intraocular lens creates myopic shift with or without astigmatism, which provides good near visual acuity.

Advantageously, because only a monofocal optic is required, the halos, glare, and/or compromised near visual acuity found with conventional multifocal lenses is substantially reduced or eliminated. The hinge system found with accommodating intraocular lenses is also eliminated.

BRIEF DESCRIPTION OF DRAWINGS

For a more complete understanding of the present invention, and the advantages thereof, reference is now made to the following descriptions taken in conjunction with the accompanying drawings, in which.

DETAILED DESCRIPTION OF THE INVENTION

The principles of the present invention and their advantages are best understood by referring to the illustrated embodiment depicted in FIGS. 1-5 of the drawings, in which like numbers designate like parts.

Figure 1:
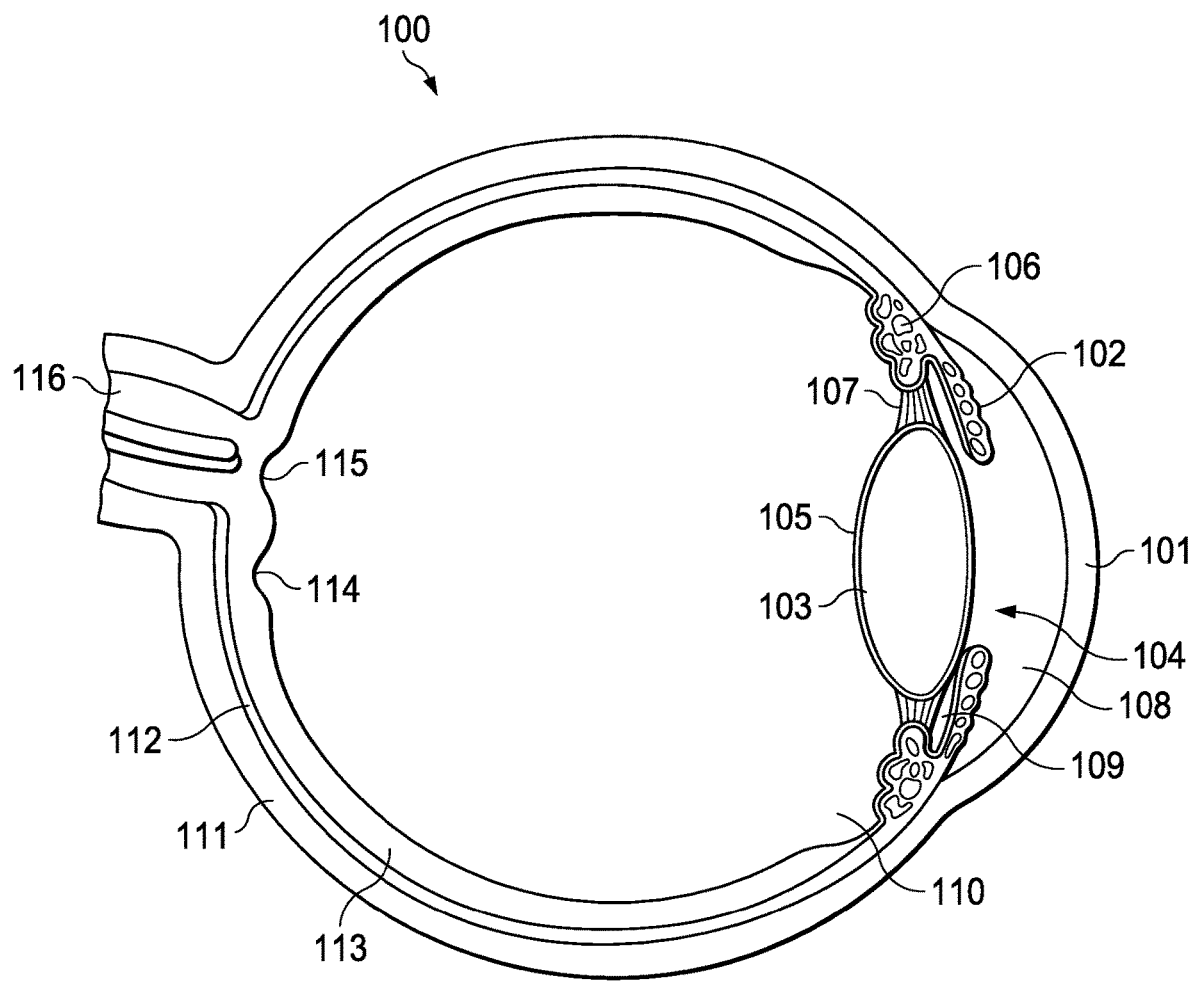
FIG. 1 is a cross-sectional diagram showing the basic anatomy of the human eye.

FIG. 1 is a cross-sectional diagram illustrating the basic anatomy of a typical human eye 100. The primary structures include the cornea 101, iris 102, crystalline lens 103, and pupil 104. Lens 103 is enclosed by the capsular bag 105, which is supported by suspensory ligaments 107. The ciliary body 106 includes the ciliary muscle that controls focusing of capsular bag 105. The anterior chamber 108 spaces cornea 101 from the anterior portion of lens 103 and the anterior portion of iris 102. The posterior chamber 109 is disposed between the posterior portion of iris 102 and suspensory ligaments 107. The vitreous body 110 is disposed behind the posterior portion of capsular bag 105.

The sclera 111 or "white" of the eye provides the outer supporting wall of the eye and is continuous with cornea 101. The choroid 112 is disposed between sclera 111 and the retina 113. The rear of the eye includes the macula lutea 114 and the optic disc 115 at the point of entry of the optic nerve 116.

In a typical aphakic implantation of an intraocular lens, the surgeon makes an incision at the point where sclera 111 meets cornea 101. The surgeon then cuts a circular opening into the anterior portion of capsular bag 105 (capsulorrhexis) and makes a viscoelastic injection to maintain the shape and pressure of the eye. Fluid is injected to separate lens 103 from capsular bag 105 (hydrodissection). Next, a phaco probe is inserted through the incision and the cataract and lens are broken into pieces using ultrasound provided by a phacoemulsifier. The phacomulsifier also removes the pieces of the lens and cataract by suction. The rear inside surface of capsular bag 105 may also be polished.

The intraocular lens is now inserted into the remaining portion of capsular bag 105. There are a number of commercially available lens designs, including multiple piece (i.e., optic and haptics of different material), single piece (i.e., optic and haptics made integrally of the same material), and plate haptic, among others. The lens is commonly folded for insertion by injection using a lens injector probe.

Figure 2:
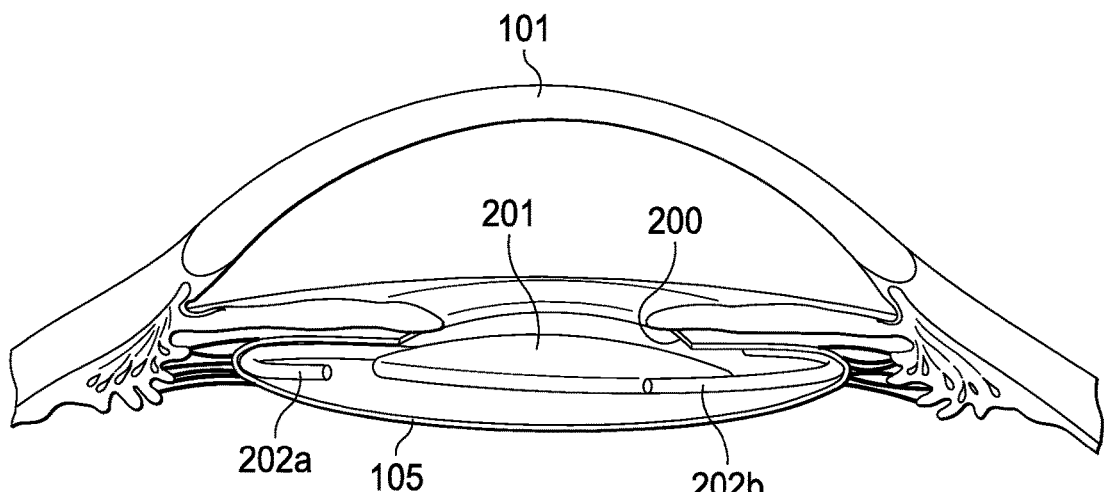
FIG. 2 is a cross-sectional diagram showing a portion of a human eye in which a representative conventional intraocular lens has been implanted using conventional techniques.

After injection, the implanted intraocular lens is held in place by the haptic or haptics, depending on the lens design. FIG. 2 shows an exemplary implanted intraocular lens including the optic 201 and haptics 202a and 202b. Optic 201 aligns with the aperture 200 formed in the anterior portion of capsular bag 104, as well as iris 102. Haptics 202a-202b extend concentrically outward from optic 201 to contact the inner wall of capsular bag 105 and hold optic 201 in place.

Typically, capsular bag 105 collapses onto the implanted intraocular lens such that the lens does not move within capsular bag 105. In contrast, according to the principles of the present invention, at least the optic portion of the intraocular lens is disposed within its own inner capsular bag, which is then disposed within natural capsular bag 105. Although natural capsular bag 105 may collapse on the surface of the inner capsular bag, the intraocular lens is still allowed to tilt and move forwards within the inner capsular bag.

Advantageously, when the patient tilts his or her head down, for example to read, the optic tilts as well, creating a myopic shift with or without astigmatism (near sightedness). The myopic astigmatism allows the patient good near visual acuity even with a monofocal lens designed for distance visual acuity. In other words, the ability to tilt and move forwards allows a monofocal lens to operate as a multifocal lens, without the multiple zones and attendant problems with halos, glare, and near focusing clarity found with typical multifocal lenses. In addition, the hinges, as well as problems with variable near visual acuity, found with accommodating lenses, are eliminated.

FIGS. 3A-3F are a series of views of a representative intraocular lens-inner capsular bag system 300 embodying the principles of the present invention. According to these principles, an inner (artificial) capsular bag is implanted within the natural capsular bag of the eye. The inner capsular bag preserves a space within which at least a part of an intraocular lens is allowed to tilt and move forwards in response to tilting downward of the patient's head. When the patient's head tilts downward, the tilting of the intraocular lens produces near focusing, and while the patient's head is substantially level, the substantially vertical disposition of intraocular lens provides distance focusing.

Figure 3A:
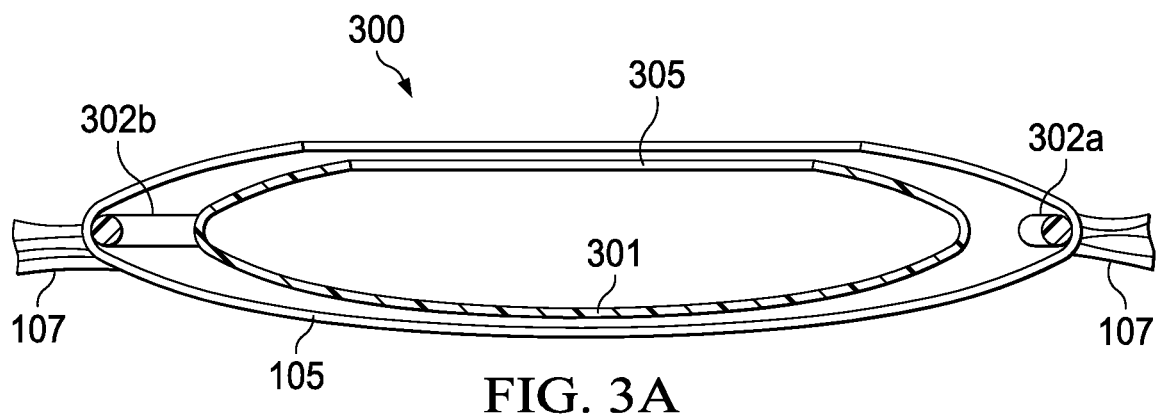
FIG. 3A is a side cross-sectional view of the natural capsular bag of a human eye implanted with an inner (artificial) capsular bag forming a part of an intraocular lens-inner capsular bag system according to one representative embodiment of the principles of the present invention.
Figure 3B:
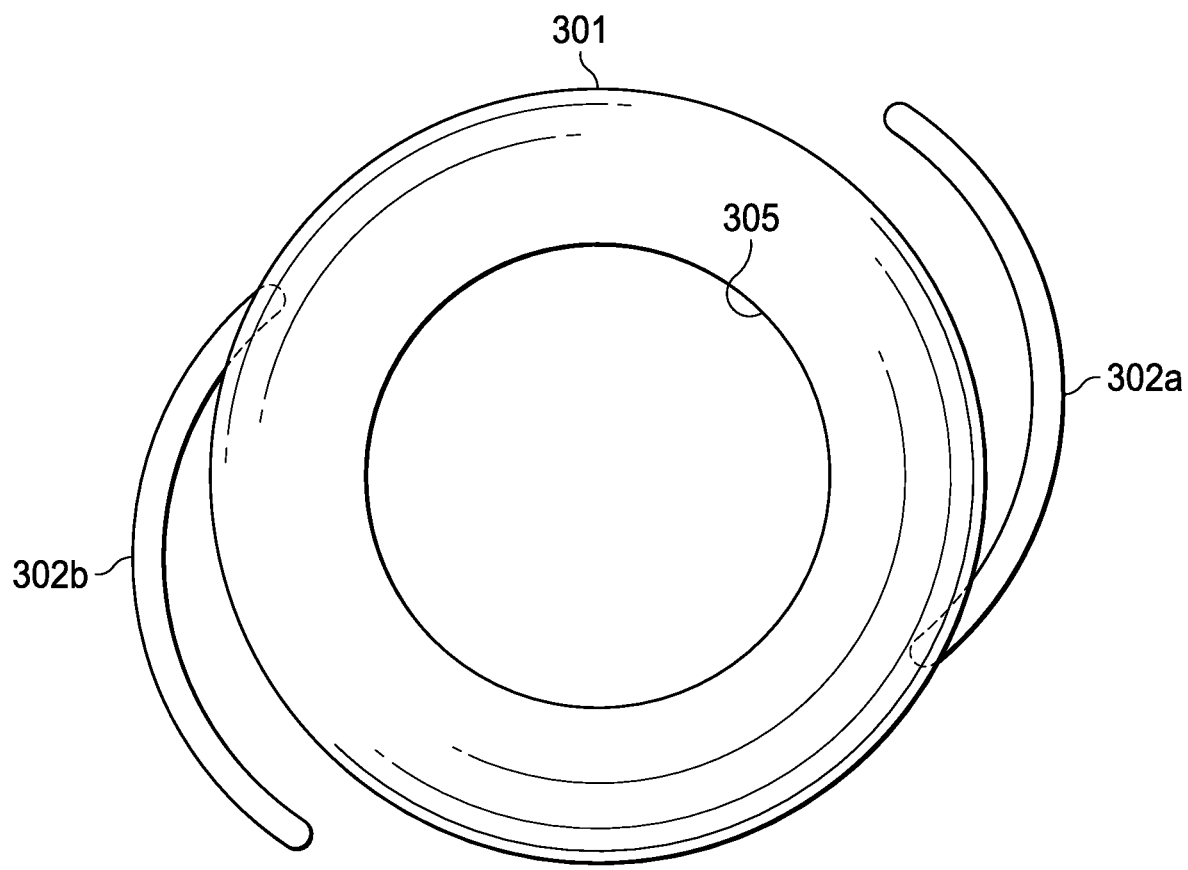
FIG. 3B is a top plan view of the inner capsular bag of FIG. 3A.

As shown in FIGS. 3A and 3B, intraocular lens-inner capsular bag system 300 includes an inner (artificial) capsular bag 301 having a pair of haptics 302a and 302b, which retain inner capsular bag 301 against the inner surface of natural capsular bag 105 (FIG. 3A).

While haptics 302a-302b in the embodiment of FIGS. 3A and 3B have a shallow arc-shape, any one of a number of known haptic designs may be used in actual practice of the inventive principles. Haptics 302a-302b may be fabricated as an integral piece with inner capsular bag 301 or be fabricated as separate pieces. Preferably the assembly of inner capsular bag 301 and haptics 302 is foldable to allow injection into natural capsular bag 105.

Figure 3C:
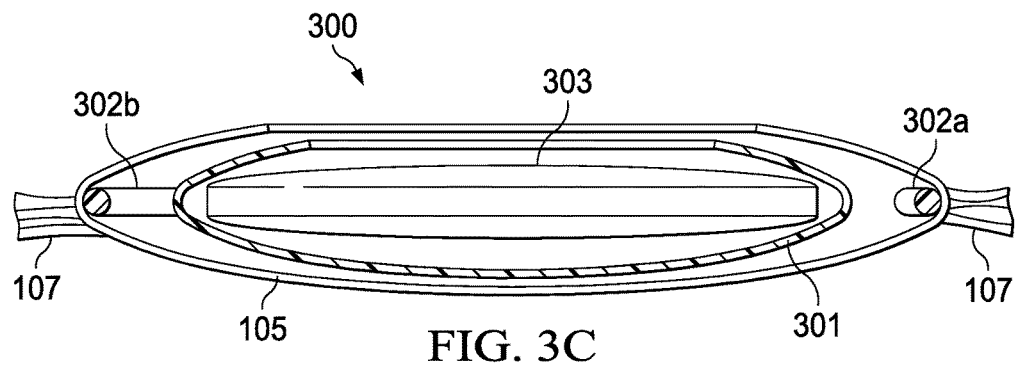
FIG. 3C is a side cross-sectional view showing the complete intraocular lens-inner capsular bag system implanted within the natural capsular bag of a human eye.
Figure 3D:
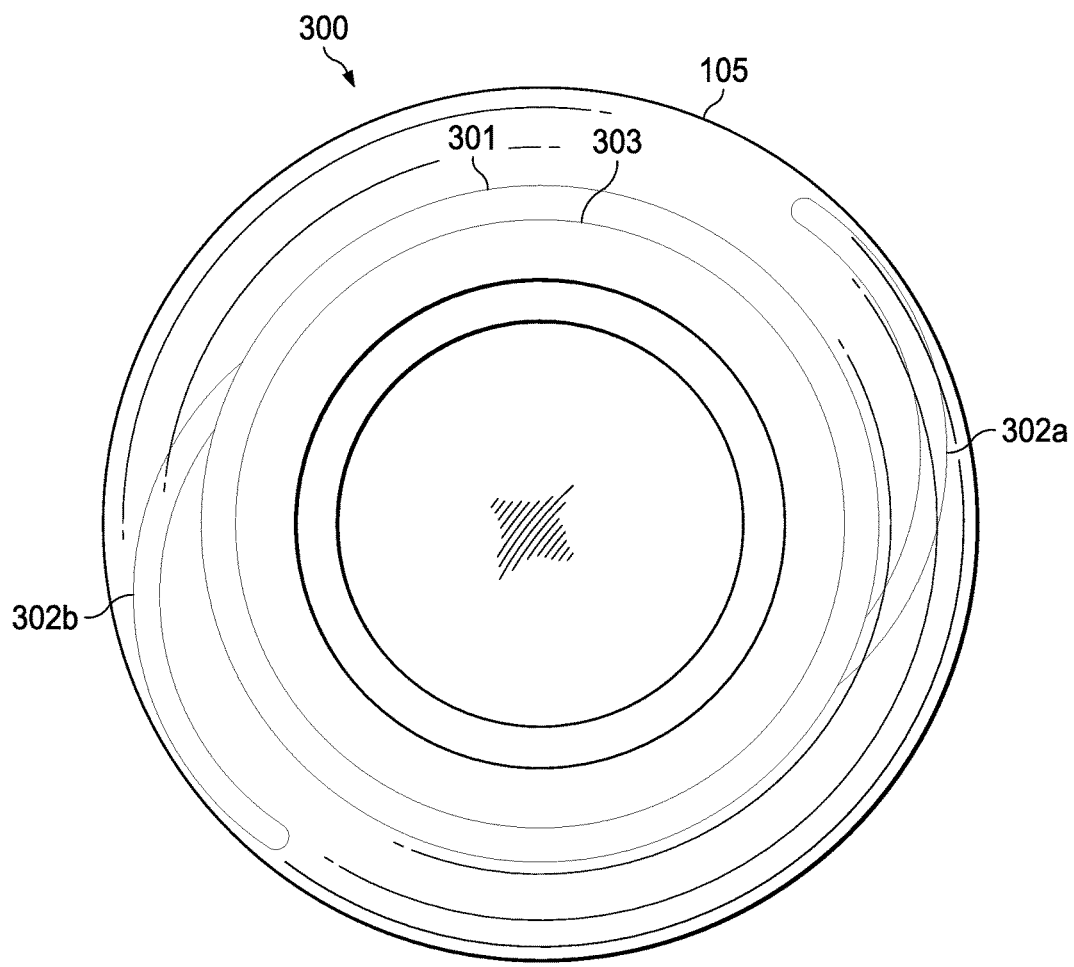
FIG. 3D is a top plan view showing the complete intraocular-lens system of FIG. 3C implanted within the natural capsular bag of a human eye.

FIGS. 3C and 3D show the complete intraocular-lens system 300 of FIGS. 3C and 3D implanted within the natural capsular bag 105 of the eye. Complete intraocular-lens system of 300 includes an intraocular lens 303 disposed within inner bag 301. As discussed below, the space preserved around intraocular lens 303 by inner bag 301 allows at least part of intraocular lens 303 to tilt and move forwards in response to gravity. The anterior portion of bag 301 includes an aperture 305, which is nominally 6 mm in diameter, but could be larger for larger (myopic) eyes.

Inner bag 301 is fabricated using any one of a number of available biocompatible materials and is "shrink wrapped" by the natural capsular bag, which is adheres to, although inner bag 301 does not adhere to the surfaces of intraocular lens 303, which allows intraocular lens to "float" or "tilt" inside it. Representative materials suitable for fabricating inner capsular bag 301, as well as intraocular lens 302, include polymethyl methacrylate, silicon, hydrophobic or hydrophilic acrylic, or collamer (e.g., a combination of collagen and polymer).

Intraocular lens 303 is preferably a monofocal lens, although any type of lens may be used, such as toric, spherical, and aspheric, as needed to provide distance visual acuity when the patient is looking straight ahead (i.e., intraocular lens 302 is not titled) and near visual acuity provided by creating a myopic shift with or without astigmatism, when the patient is looking downward (i.e., intraocular lens 302 is tilted and forward).

Figure 4A:
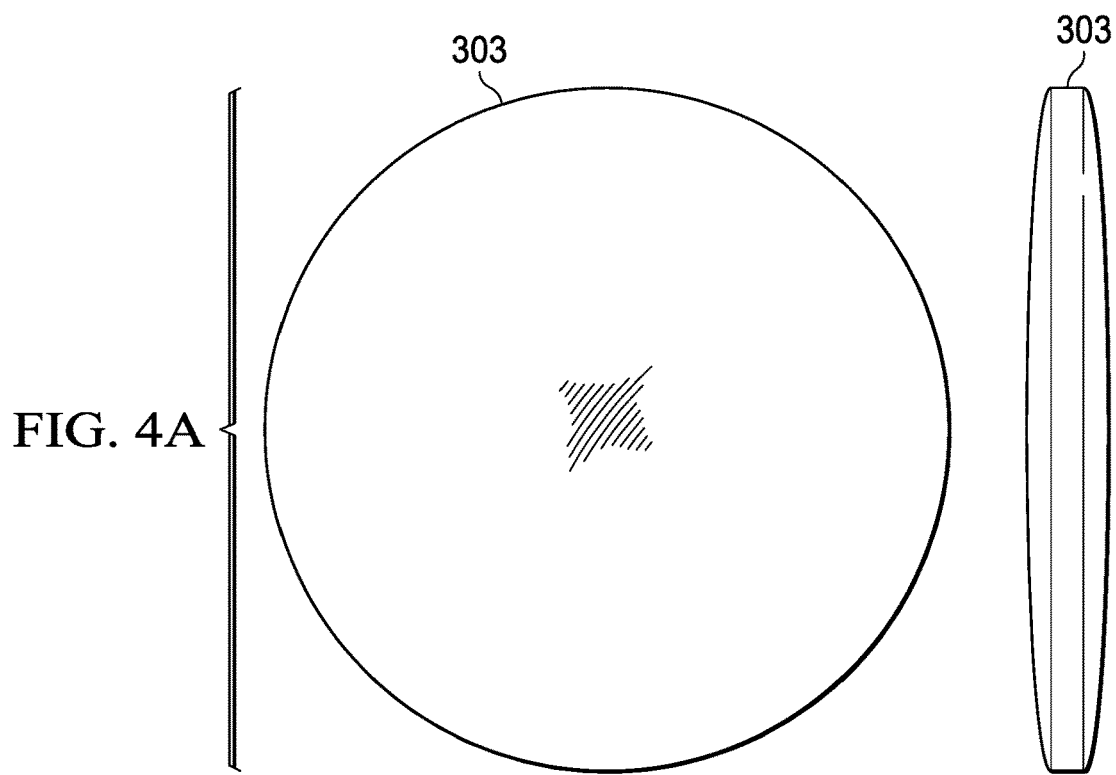
FIG. 4A provides top plan and side elevational views of a exemplary spherical lens suitable for use in the intraocular-lens system of FIGS. 3C and 3D.
Figure 4B:
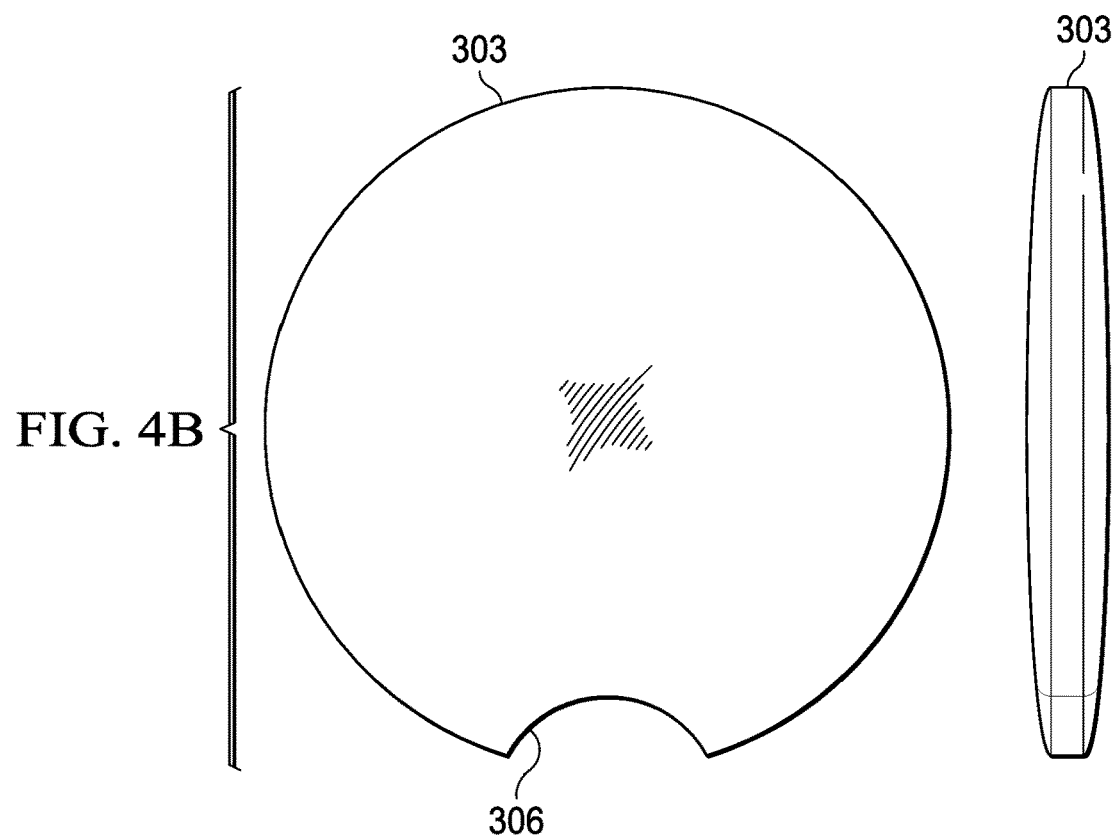
FIG. 4B provides top plan and side elevational views of an exemplary toric lens suitable for use in the intraocular-lens system of FIGS. 3C and 3D.

FIG. 4A shows a representative spherical embodiment of lens 303 having a nominal diameter of 7 mm. FIG. 4B is a representative toric embodiment of lens 303, having a nominal diameter of 7 mm and a notch 306 for preventing rotation. Lens 303 may optionally be back-weighted at the vertical edge, as necessary to improve tilting and forward motion within inner bag 301.

Figure 3E:
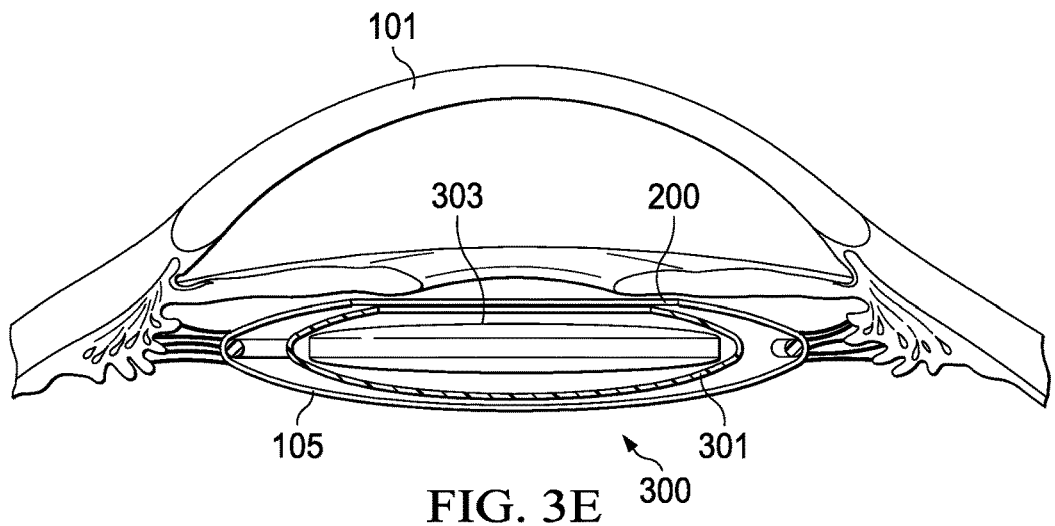
FIG. 3E is a side cross-sectional view showing the complete intraocular-lens system of FIGS. 3C and 3D implanted within a human eye.

FIG. 3E is a cross-sectional view of a human eye into which intraocular lens-inner bag system 300 been implanted. Inner capsular bag 301 is retained in natural capsular bag 301 by haptics 302. After surgery, natural capsular bag 105 collapses around the surfaces of inner capsular bag 301, although optic lens 303 can still tilt and move forward with in inner capsular bag 401.

Figure 3F:
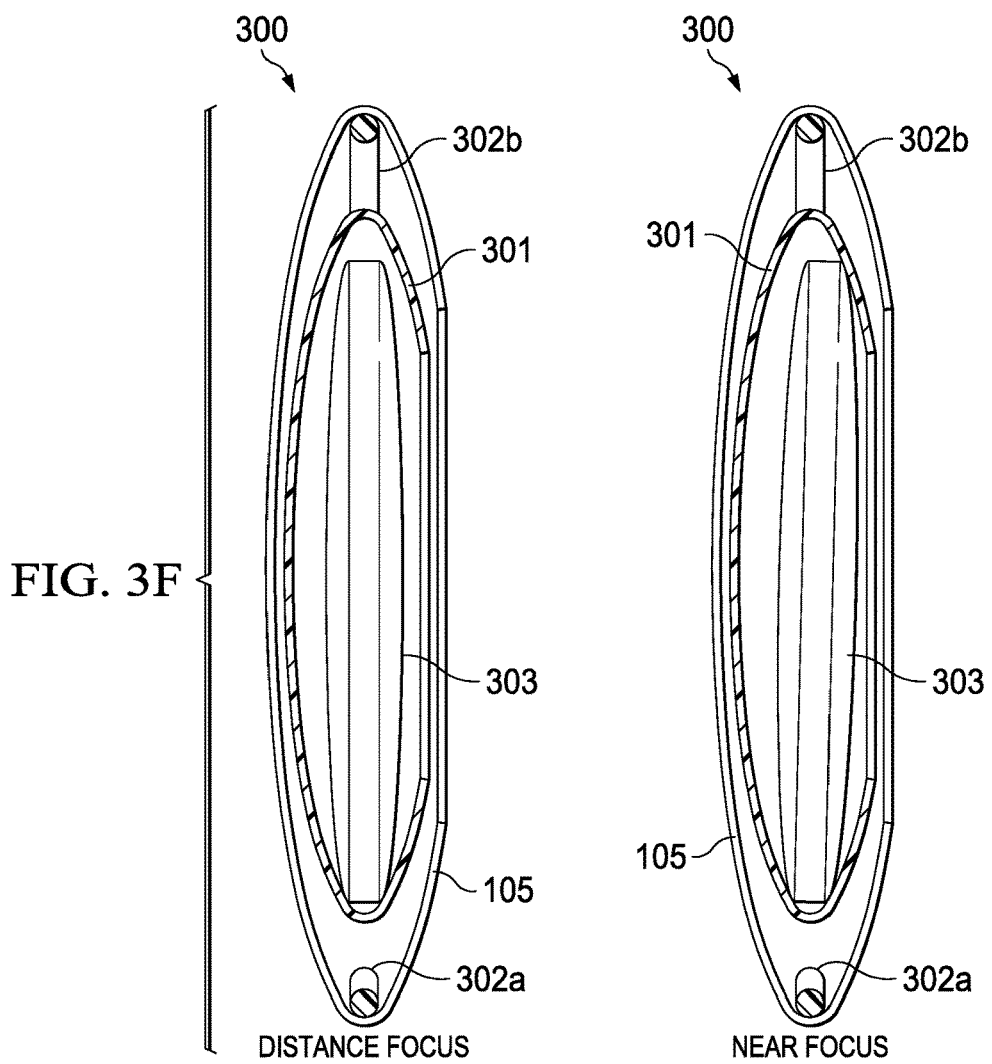
FIG. 3F provides side cross-sectional views illustrating the functioning of the intraocular lens-inner capsular bag system of FIGS. 3C and 3D when providing distance focusing and near focusing.

FIG. 3F is a conceptual drawing showing the positioning of optic 303 for both distance and near focus. In particular, for distance focusing, with the patient's head generally parallel to the ground, optic 303 is maintained by gravity in a substantially vertical position. For near focusing, when the patient's head tilted downward, gravity tilts/moves optic 403 forward, with respect to the cornea and retina, which creates a myopic shift with or without astigmatism. In the preferred embodiment, inner bag 301 and lens 303 are dimensioned to allow lens 303 to tilt between 1 to 2 mm when the patient is looking downward.

Figure 5A:
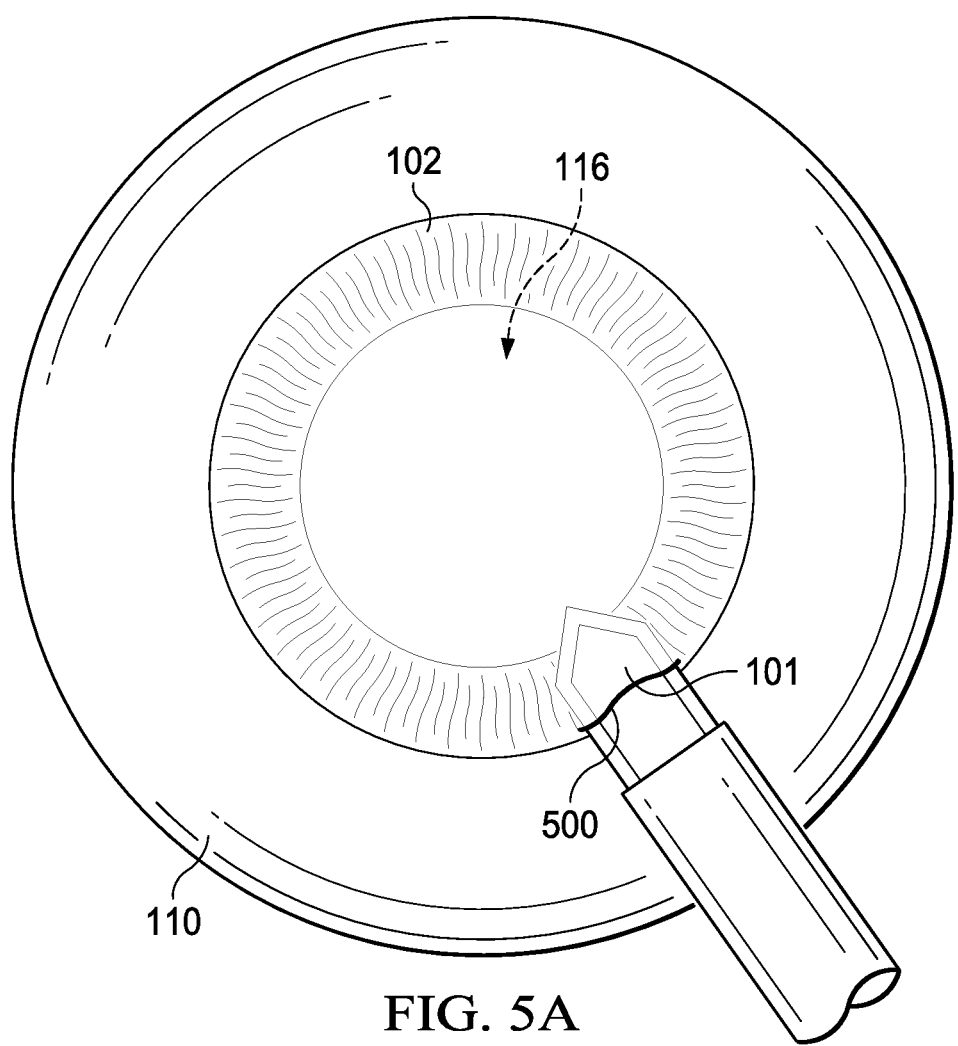
FIGS. 5A-5E illustrate a representative procedure for implanting an intraocular lens according to the principles of the present invention.
Figure 5B:
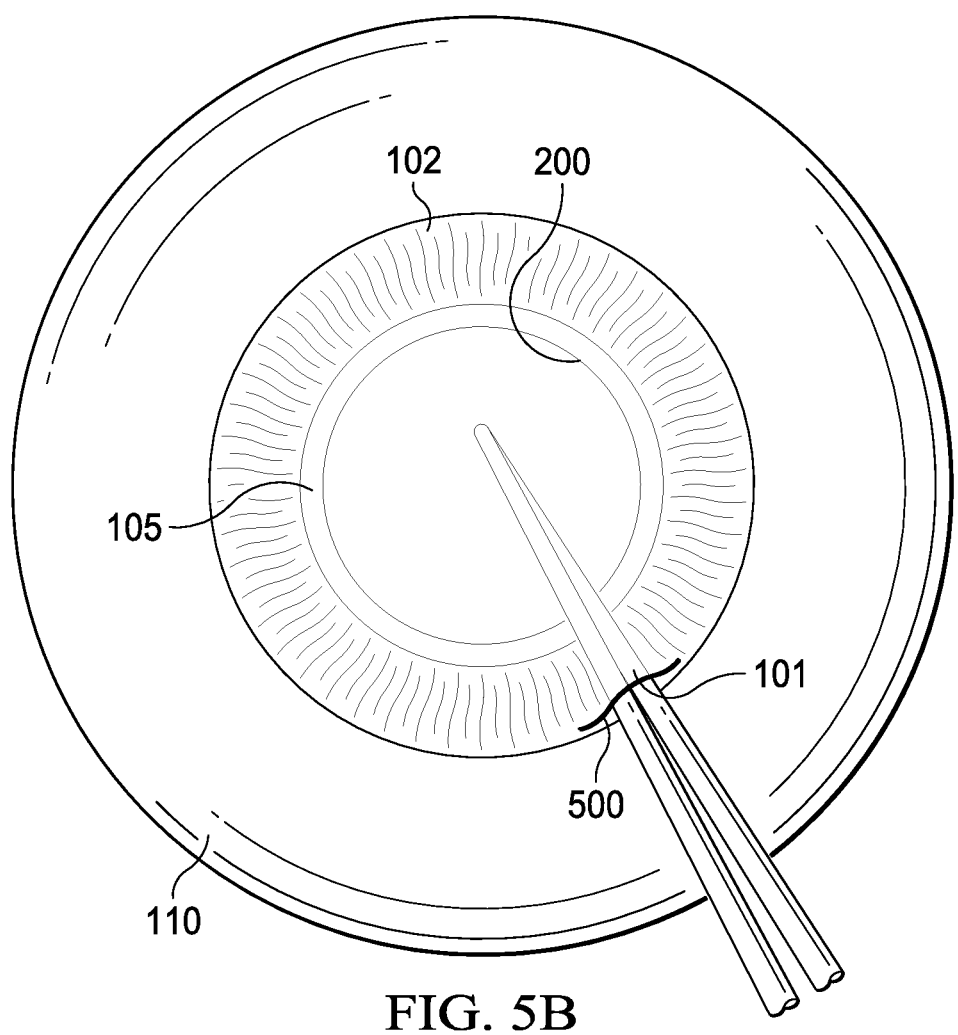

FIGS. 5A-5B are a set of diagrams illustrating one procedure for implanting either intraocular lens-inner capsular bag system 300. In the preferred embodiment of the present principles, the inner capsular bag is inserted first into the natural capsular bag, followed by the insertion of the intraocular lens into the inner capsular bag. However, in alternate embodiments, the inner capsular bag, along with the enclosed intraocular lens, could be inserted together into the natural capsular bag as one piece.

As shown in FIG. 5A, a micro-incision 500 is made at the point where the cornea 101 meets the sclera 110. A viscoelastic injection is made through the incision to maintain the shape and pressure of the eye.

Figure 5C:
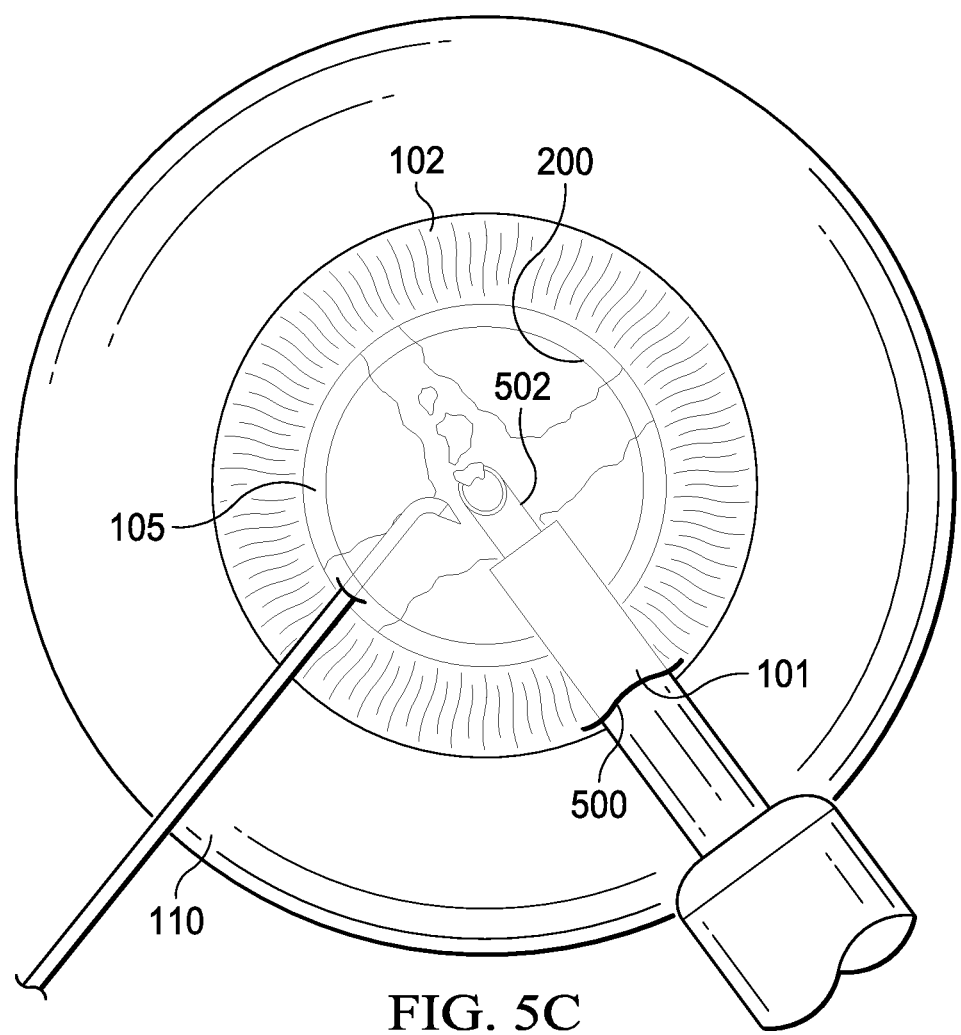

In FIG. 5B, an opening 200 is made through the anterior surface of capsular bag 105 (capsulorrhexis). The back of natural capsular bag 105 may also be polished after complete removal of the natural bag. As shown in FIG. 5C the tip 502 of a phaco probe is then inserted through micro-incision 500 and natural lens 103 and any cataract is broken into small pieces using a phacoemulsifier, which also suctions those pieces out through phaco tip 502.

Figure 5D:
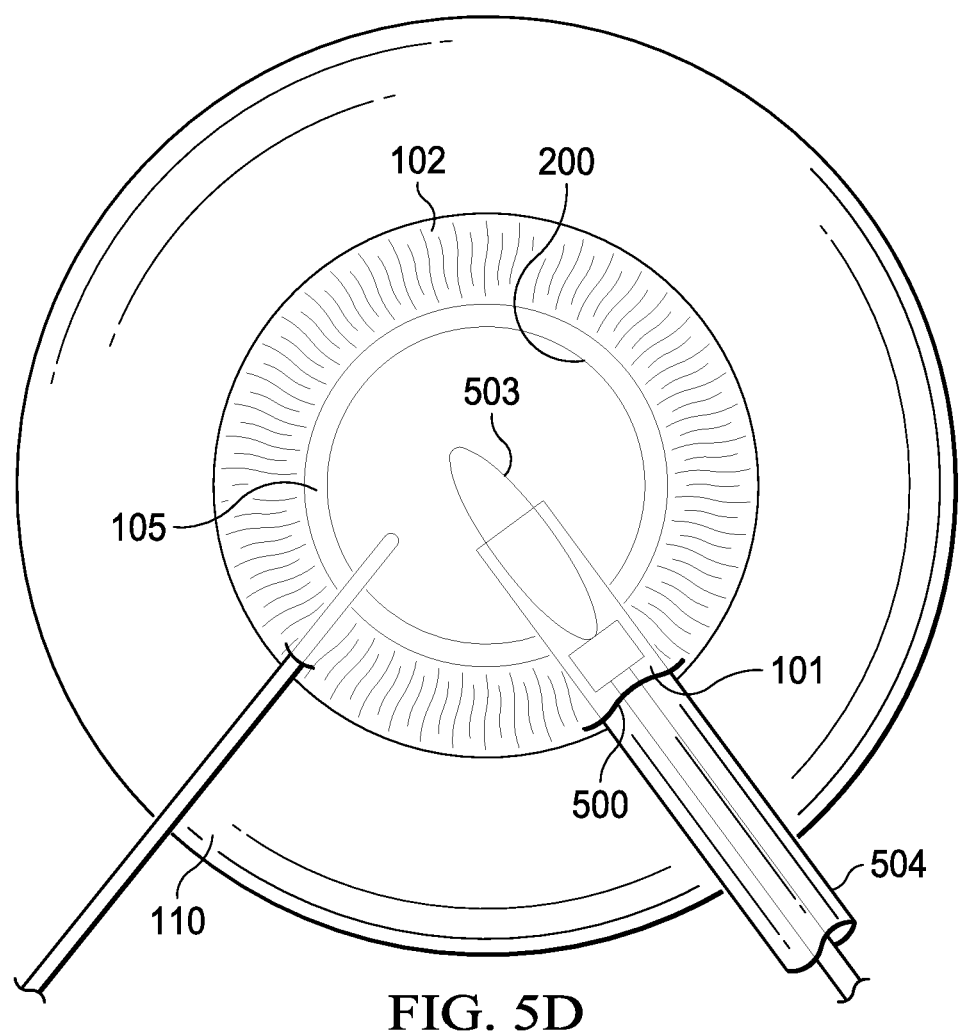
Figure 5E:
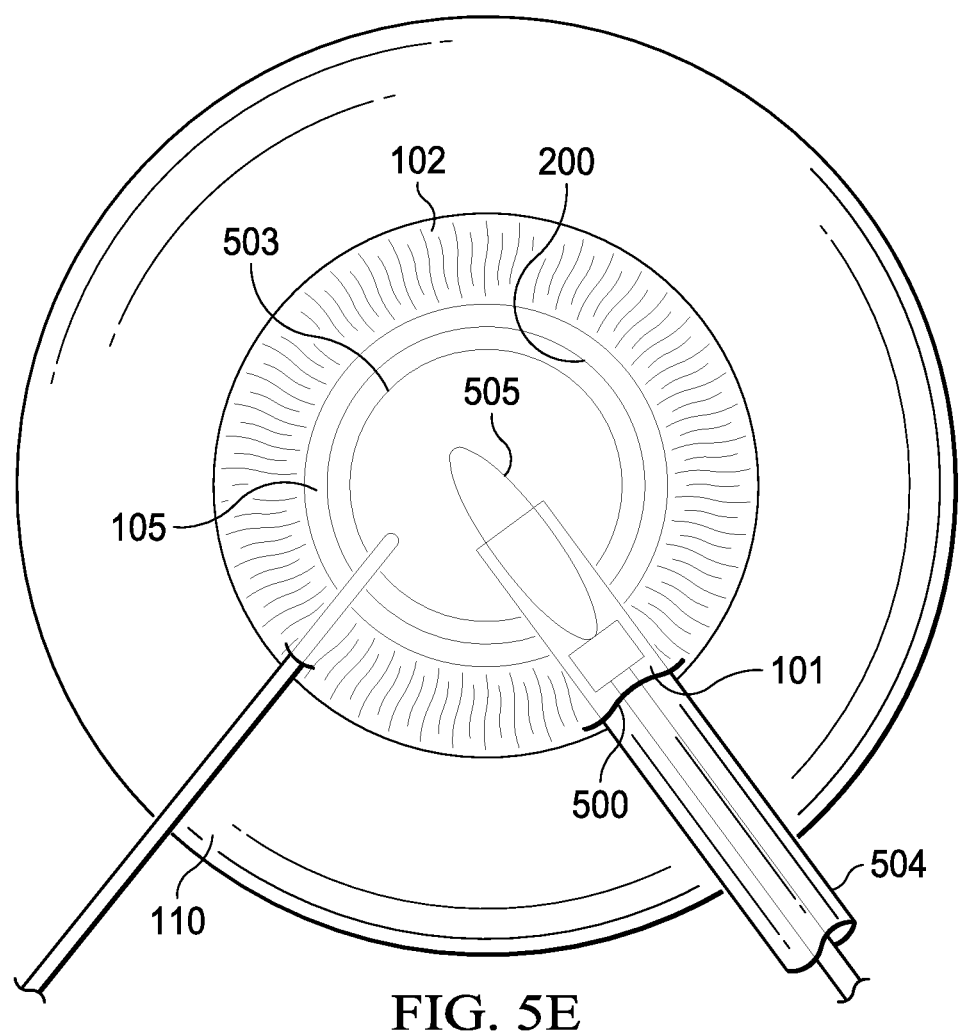

The inner capsular bag 503, such as inner capsular bag 301 of system 300 or inner capsular bag 401 of system 400, is injected using lens injector 504 as shown in FIGS. 5D and 5E. Intraocular lens 505, such as intraocular lens 302 of system 300 or optic lens 403 of system 400, is then injected into inner capsular bag 503. (Prior to surgery, the power of intraocular lens 505 was determined using standard methods.)

The procedure shown in FIGS. 5A-5E is only one of a number of possible procedures available for implementing the principles of the present invention. Generally, the selected procedure is one that safely and efficiently allows for the implantation of an intraocular lens-inner capsular bag system, which includes an inner artificial capsular bag and enclosed intraocular lens, into the natural capsular bag of an eye.

Although the invention has been described with reference to specific embodiments, these descriptions are not meant to be construed in a limiting sense. Various modifications of the disclosed embodiments, as well as alternative embodiments of the invention, will become apparent to persons skilled in the art upon reference to the description of the invention. It should be appreciated by those skilled in the art that the conception and the specific embodiment disclosed might be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore contemplated that the claims will cover any such modifications or embodiments that fall within the true scope of the invention.

I claim:

1. An intraocular lens system comprising:
    an artificial capsular bag adapted for implantation within a natural capsular bag of an eye, the artificial capsular bag being adapted to preserve a space when the natural capsular bag collapses around the artificial capsular bag following implantation; and
    an intraocular lens adapted to be received within the artificial capsular bag, the space preserved by the artificial capsular bag allowing the intraocular lens to tilt toward the eye's cornea without having to move upwardly under gravitational force, wherein the tilt of the intraocular lens results in an upper part of the intraocular lens being closer to the cornea than a lower portion of the intraocular lens, thereby causing a myopic shift.

2. The intraocular lens system of claim 1, wherein the artificial capsular bag comprises at least one haptic for retaining the artificial capsular bag within the natural capsular bag.

3. The intraocular lens system of claim 2, wherein the at least one haptic is formed integrally with the artificial capsular bag.

4. The intraocular lens system of claim 2, wherein the artificial capsular bag is foldable.

5. The intraocular lens system of claim 1, wherein the intraocular lens comprises a monofocal lens.

6. The intraocular lens system of claim 1, wherein the intraocular lens comprises spherical lens.

7. The intraocular lens system of claim 1, wherein the intraocular lens comprises a toric lens.

8. The intraocular lens system of claim 1, wherein artificial capsular bag is fabricated from a material selected from the group consisting of polymethyl methacrylate, silicon, hydrophobic acrylic, hydrophilic acrylic, and collamer.

9. A method of correcting vision comprising:
    implanting, within the natural capsular bag of an eye, an inner capsular bag and an intraocular lens within inner capsular bag, the inner capsular bag allowing the intraocular lens to tilt in response to gravity within a space preserved by the inner capsular bag after the natural capsular bag collapses around the inner bag following implantation, the tilt of the intraocular lens causing an upper part of the intraocular lens to move closer toward the cornea of the eye than a lower portion of the lens, thereby creating a myopic shift without the lens shifting upwardly.

10. The method of claim 9, wherein implanting comprises:
  inserting the inner capsular bag into the natural capsular bag; and
  inserting the intraocular lens into the inner capsular bag after the inner capsular bag has been inserted into the natural capsular bag.

11. The method of claim 9, wherein implanting comprises:
  inserting the intraocular lens into the inner capsular bag; and
  inserting the inner capsular bag and the movable intraocular lens together into the natural capsular bag.

12. The method of claim 9, wherein implanting comprises injecting at least one of the inner capsular bag and the intraocular lens.

13. The method of claim 9, wherein implanting comprises disposing a spherical lens within the inner capsular bag.

14. The method of claim 9, wherein implanting comprises disposing a toric lens within the inner capsular bag.

15. A vision correction system comprising:
  an inner bag fabricated of a biocompatible material and adapted for implantation within a natural capsular bag of an eye; and
  an intraocular lens adapted to be received within the inner bag, the inner bag allowing, when implanted, the intraocular lens to tilt toward a cornea of the eye within the inner bag and causing an upper part of the intraocular lens to move closer to the cornea than a lower portion of the intraocular lens in response to gravitational force, thereby creating a myopic shift without the lens shifting upwardly.

16. The vision correction system of claim 15, wherein the inner bag is retained in the natural capsular bag by at least one haptic.

17. The vision correction system of claim 15, wherein the intraocular lens comprises a monofocal lens.

18. The vision correction system of claim 15, wherein the intraocular lens comprises a spherical lens.

19. The vision correction system of claim 15, wherein the intraocular lens comprises a toric lens.

20. The vision correction system of claim 15, wherein, the inner bag is fabricated from a material selected from the group consisting of polymethyl methacrylate, silicon, hydrophobic acrylic, hydrophilic acrylic, and collamer.

* * * * *